US011191951B2

(12) United States Patent
Haralambidis

(10) Patent No.: US 11,191,951 B2
(45) Date of Patent: *Dec. 7, 2021

(54) DEVICE FOR ELECTRICAL STIMULATION OF PERIODONTAL COMPLEX AND SURROUNDING TISSUE

(71) Applicant: Cosmo Haralambidis, Cranston, RI (US)

(72) Inventor: Cosmo Haralambidis, Cranston, RI (US)

(*) Notice: Subject to any disclaimer, the term of this patent is extended or adjusted under 35 U.S.C. 154(b) by 173 days.

This patent is subject to a terminal disclaimer.

(21) Appl. No.: 16/540,112

(22) Filed: Aug. 14, 2019

(65) Prior Publication Data

US 2019/0366075 A1    Dec. 5, 2019

Related U.S. Application Data

(63) Continuation of application No. 15/791,462, filed on Oct. 24, 2017, now Pat. No. 10,391,302, which is a (Continued)

(51) Int. Cl.
*A61N 1/05* (2006.01)
*A61N 1/36* (2006.01)
(Continued)

(52) U.S. Cl.
CPC ............ *A61N 1/0548* (2013.01); *A61C 19/06* (2013.01); *A61N 1/0472* (2013.01); *A61N 1/36021* (2013.01)

(58) Field of Classification Search
CPC ............................ A61N 1/0548; A61N 1/36021
(Continued)

(56) References Cited

U.S. PATENT DOCUMENTS 1,525,857 A    2/1925    Eidmann
2,151,738 A    3/1939    Buhse
(Continued)

FOREIGN PATENT DOCUMENTS

CA    2999710 A1    11/2016
CN    1972729 A     5/2007
(Continued)

OTHER PUBLICATIONS

Abd-Elmeguid, et al., "Dental Pulp Neurophysiology: Part 1. Clinical and Diagnostic Implications", JCDA, URL: www.cda-adc.ca/jcda, vol. 75, No. 1, Feb. 2009, pp. 55-59.
(Continued)

*Primary Examiner* — Nadia A Mahmood

(57) ABSTRACT

A device for electrical stimulation of one or more components of the periodontal complex and surrounding tissue of a tooth, for uses such as reducing orthodontic pain and encouraging tooth movement, has electrodes of a rigid, electrically conductive material in a fixed spatial relationship configured for application to oral mucosa and attached gingiva adjacent to, and along a periodontal ligament of, a root structure of a single tooth. An electrical circuit is configured for electrical connection to the at least two electrodes. The electrical circuit has an output providing a subsensory electrical stimulus comprising a waveform in accordance with predetermined stimulation parameters. After the electrodes are applied to the oral mucosa and attached gingiva adjacent to, and along the periodontal ligament of, a root structure of the tooth, a switch, when activated, activates the electrical circuit to output the electrical stimulus through the at least two electrodes.

18 Claims, 9 Drawing Sheets

Related U.S. Application Data continuation of application No. 15/147,234, filed on May 5, 2016, now Pat. No. 9,855,418.

(60) Provisional application No. 62/157,053, filed on May 5, 2015.

(51) Int. Cl.
*A61C 19/06* (2006.01)
*A61N 1/04* (2006.01)

(58) Field of Classification Search
USPC .............................................. 607/9, 47, 152
See application file for complete search history.

(56) References Cited

U.S. PATENT DOCUMENTS

| | | | |
|---|---|---|---|
| 3,502,076 A | 3/1970 | Bertolini |
| 3,955,583 A | 5/1976 | Horauf |
| 4,055,190 A | 10/1977 | Tany et al. |
| 4,109,660 A | 8/1978 | Nesmeyanov et al. |
| 4,147,171 A | 4/1979 | Greene et al. |
| 4,153,060 A | 5/1979 | Korostoff et al. |
| 4,177,819 A | 12/1979 | Kofsky et al. |
| 4,244,373 A | 1/1981 | Nachman |
| 4,535,777 A | 8/1985 | Castel |
| 4,550,733 A | 11/1985 | Liss et al. |
| 4,553,549 A | 11/1985 | Pope et al. |
| 4,590,942 A | 5/1986 | Man et al. |
| 4,676,257 A | 6/1987 | Halpern |
| 4,782,837 A | 11/1988 | Hogan |
| 4,784,142 A | 11/1988 | Liss et al. |
| 4,854,865 A | 8/1989 | Beard et al. |
| 4,924,880 A | 5/1990 | O'Neill et al. |
| 5,018,525 A | 5/1991 | Konobevtsev et al. |
| 5,052,391 A | 10/1991 | Silberstone et al. |
| 5,067,495 A | 11/1991 | Brehm |
| 5,304,207 A | 4/1994 | Stromer et al. |
| 5,387,231 A | 2/1995 | Sporer |
| 5,571,149 A | 11/1996 | Liss et al. |
| 5,607,461 A | 3/1997 | Lathrop |
| 5,620,483 A | 4/1997 | Minogue |
| 5,626,628 A | 5/1997 | Ganansia et al. |
| 5,974,342 A | 10/1999 | Petrofsky |
| 6,212,435 B1 | 4/2001 | Lattner et al. |
| 6,249,706 B1 | 6/2001 | Sobota et al. |
| 6,595,775 B1 | 7/2003 | Berk et al. |
| 6,684,639 B2 | 2/2004 | Ichinose et al. |
| 6,832,912 B2 | 12/2004 | Mao et al. |
| 7,029,276 B2 | 4/2006 | Mao et al. |
| 8,165,668 B2 | 4/2012 | Zipfel et al. |
| 8,602,777 B2 | 12/2013 | Bryce et al. |
| 8,770,969 B2 | 7/2014 | Abatelli et al. |
| 8,909,346 B2 | 12/2014 | Chalmers et al. |
| 8,948,864 B2 | 2/2015 | Colthurst |
| 9,028,250 B2 | 5/2015 | Lowe et al. |
| 9,061,148 B2 | 6/2015 | Bachinski et al. |
| 9,119,963 B1 | 9/2015 | Al-Shemmeri |
| 9,242,118 B2 | 1/2016 | Brawn |
| 9,662,183 B2 | 5/2017 | Lowe et al. |
| 9,855,418 B2 | 1/2018 | Haralambidis |
| 9,895,539 B1 | 2/2018 | Heit et al. |
| 10,391,302 B2 | 8/2019 | Haralambidis |
| 2001/0034544 A1 | 10/2001 | Mo |
| 2003/0018367 A1 | 1/2003 | DiLorenzo et al. |
| 2004/0044338 A1 | 3/2004 | Lennox et al. |
| 2004/0267333 A1 | 12/2004 | Kronberg et al. |
| 2007/0276449 A1 | 11/2007 | Gunter et al. |
| 2008/0227046 A1 | 9/2008 | Lowe et al. |
| 2008/0233541 A1 | 9/2008 | De et al. |
| 2009/0117513 A1 | 5/2009 | Nemeh et al. |
| 2010/0055634 A1 | 3/2010 | Spaulding et al. |
| 2010/0312233 A1 | 12/2010 | Furnish et al. |
| 2012/0148975 A1 | 6/2012 | Brawn et al. |
| 2013/0013028 A1 | 1/2013 | Kriksunov et al. |
| 2013/0066394 A1 | 3/2013 | Saab et al. |
| 2013/0085551 A1 | 4/2013 | Bachinski et al. |
| 2013/0196284 A1 | 8/2013 | Brawn et al. |
| 2013/0209964 A1 | 8/2013 | Nemeh et al. |
| 2013/0280671 A1 | 10/2013 | Brawn et al. |
| 2014/0023983 A1 | 1/2014 | Lowe et al. |
| 2014/0072932 A1 | 3/2014 | Brawn et al. |
| 2014/0081256 A1 | 3/2014 | Carmel et al. |
| 2014/0194946 A1 | 7/2014 | Thomas et al. |
| 2014/0194949 A1 | 7/2014 | Wichner et al. |
| 2014/0277323 A1 | 9/2014 | Tingey |
| 2014/0316310 A1 | 10/2014 | Ackermann et al. |
| 2016/0001082 A1 | 1/2016 | Butera et al. |
| 2016/0022989 A1 | 1/2016 | Pfeifer |
| 2016/0045731 A1 | 2/2016 | Simon et al. |
| 2016/0325092 A1 | 11/2016 | Haralambidis |
| 2018/0104476 A1 | 4/2018 | Haralambidis |
| 2018/0369566 A1 | 12/2018 | Wainless et al. |
| 2019/0117961 A1 | 4/2019 | Haralambidis |

FOREIGN PATENT DOCUMENTS

| | | |
|---|---|---|
| CN | 101203186 A | 6/2008 |
| CN | 102438698 A | 5/2012 |
| CN | 103458823 A | 12/2013 |
| EP | 1525857 A1 | 4/2005 |
| EP | 2218477 A1 | 8/2010 |
| EP | 2384664 B1 | 2/2014 |
| EP | 3291880 A1 | 3/2018 |
| KR | 20030070226 A | 8/2003 |
| WO | 01/003768 A1 | 1/2001 |
| WO | 2005077452 A1 | 8/2005 |
| WO | 2008145724 A1 | 12/2008 |
| WO | 2010103263 A1 | 9/2010 |
| WO | 2016179363 A1 | 11/2016 |
| WO | 2018099770 A1 | 6/2018 |
| WO | 2020123732 A2 | 6/2020 |

OTHER PUBLICATIONS

Ackermann, Jr., et al., "Conduction Block of Peripheral Nerve Using High Frequency Alternating Currents Delivered through an Intrafascicular Electrode", Muscle Nerve., vol. 41, No. 1, Jan. 2010, 5 Pages.

Ackermann, Jr., et al., "Effect of Bipolar Cuff Electrode Design on Block Thresholds in High-Frequency Electrical Neural Conduction Block", IEEE Trans Neural Syst Rehabil Eng., vol. 17, No. 5, Oct. 2009, 22 pages.

Allard, et al., "Voltage-gated Sodium Channels Confer Excitability to Human Odontoblasts", Possible Role in Tooth Pain Transmission, The Journal of Biological Chemistry, vol. 281, No. 29, Sep. 29, 2006, pp. 29002-29010.

Alvarez-Arenal, et al., "Effect of Occlusal Splint and Transcutaneous Electric Nerve Stimulation on the Signs and Symptoms of Temporomandibular Disorders in Patients with Bruxism", Journal of Oral Rehabilitation, vol. 29, 2002, pp. 858-863.

Andersson, et al., "Evaluation of the Pain Suppressive Effect of Different Frequencies of Peripheral Electrical Stimulation in Chronic Pain Conditions", Acta Orthop. Scand., vol. 47, 1976, pp. 149-157.

Asadi, Mohammad Reza, et al., "Bacterial Inhibition by Electrical Stimulation", Department of Physical Therapy, Faculty of Medical Sciences, Tarbiat Modares University, Tehran, Iran, Advances in Wound Care, vol. 3, No. 2., Apr. 14, 2013, pp. 91-97.

Bauer, William, "Electrical Treatment of Severe Head and Neck Cancer Pain", Arch Otolaryngol—vol. 109, Jun. 1983, pp. 382-383.

Bhadra, et al., "Block of Mammalian Motor Nerve Conduction Using High Frequency Alternating Current", 10th Annual Conference of the International FES Society, Montreal, Canada, Jul. 2005, 3 Pages.

Bhadra, et al., "High Frequency Electrical Conduction Block of the Pudendal Nerve", J Neural Eng, vol. 3, No. 2, Jun. 2006, 14 Pages.

Burstone, et al., "Beta Titanium: A New Orthodontic Alloy", American Journal of Orthodontics, vol. 77, No. 2, Feb. 1980, pp. 121-132.

(56) References Cited

OTHER PUBLICATIONS

Cassanelli, et al., "Alteration of Membrane Permeability of Bacteria and Yeast by High Frequency Alternating Current (HFAC)", The Open Microbiology Journal, 2008, vol. 2, Apr. 15, 2008, pp. 32-37.
Chinese Patent Office, "First Office Action Received", China Application No. 201680039999.8, dated Jul. 29, 2020, 19 Pages.
European Patent Office, "Communication under Rule 71(3) Received", European Application No. 16790069.5, dated Dec. 19, 2019, 6 Pages.
European Patent Office, "Extended European Search Report", European Application No. 16790069.5, dated Dec. 13, 2018, 12 Pages.
Frankstein, "One Unconsidered Form of the Part Played by the Nervous System in the Development of Disease", Science, Downloaded from http://science.sciencemag.org/, Apr. 10, 2017, 2 Pages.
Han, et al., "Dental Implant Electrical Stimulation Healing Device", Department of Stomatology, the Chinese PLA general hospital Beijing, China, International Conference on Materials, Manufacturing and Mechanical Engineering (MMME 2016), Dec. 30-31, 2016, pp. 83-86.
Hansson, et al., "Transcutaneous Electrical Nerve Stimulation (TENS) as Compared to Placebo TENS for the Relief of Acute Oro-Facial Pain", Pain, vol. 15, No. 2, 1983, Elsevier Biomedical Press, Mar. 24, 1982, pp. 157-165.
Hughes, Jr., et al., "Response of Plasma beta-Endorphins to Transcutaneous Electrical Nerve Stimulations in Healthy Subjects", Physical Therapy, vol. 64, No. 7, Jul. 1984, pp. 1062-1066.
Japan Patent Office, "Office Action Received", Japan Application No. 2017-558378, dated Apr. 27, 2020, 7 Pages.
Kilgore, et al., "Reversible Nerve Conduction Block Using Kilohertz Frequency Alternating Current", Neuromodulation, vol. 17, No. 3, Apr. 2014, 32 Pages.
Kuzyk, et al., "The Science of Electrical Stimulation Therapy for Fracture Healing", Indian Journal of Orthopedics, Apr.-Jun. 2009, vol. 43, No. 2, Mar. 30, 2017, 12 Pages.
Long, Don M., "Electrical Stimulation for the Control of Pain", Aech Surg, vol. 122, Jul. 1977, Apr. 11, 2017, pp. 884-888.
McCullen, et al., "Application of Low-Frequency Alternating Current Electric Fields Via Interdigitated Electrodes Effects on Cellular Viability, Cytoplasmic Calcium, and Osteogenic Differentiation of Human Adipose-Derived Stem Cells", Tissue Engineering: Part C, vol. 16, No. 6, 2010, pp. 1377-1386.
Melzack, et al., "Pain Mechanisms: A new Theory", Science, vol. 150, No. 3699, Nov. 19, 1965, pp. 971-979.
Melzack, Ronald, "Prolonged Relief of pain by Brief, Intense Transcutaneous Somatic Stimulation", Pain, vol. 1, No. 4, Dec. 1975, pp. 357-373.
Mirzaii, "Antibacterial Effect of Alternating Current Against *Staphylococcus aureus* and Pseudomonas Aeroginosa", ISSN 2304-3415, Russian Open Medical Journal, vol. 4., No. 2, Article CID e0203, Mar. 20, 2015, 5 Pages.
Patel, et al., "Differential Fiber-Specific Block of Nerve Conduction in Mammalian Peripheral Nerves Using Kilohertz Electrical Stimulation", Innovative Methodology, J Neurophysiol, vol. 113, Apr. 15, 2015, pp. 3923-3929.
Petrofsky, et al., "Effect of Electrical Stimulation on Bacterial Growth", 21 Pages.
Roth, Peter M., et al., "Effect of transcutaneous electrical nerve stimulation for controlling pain associated with orthodontic tooth movement", Am. J. Orthod. Dentofac. Orthop., vol. 90, No. 2, Aug. 1986, pp. 132-138.
Russian Fedration, "International Search Report and Written Opinion Received", Application No. PCT/US2016/030922, dated Sep. 8, 2016, 9 Pages.
Spadari, et al., "Electrical Stimulation Enhances Tissue Reorganization During Orthodontic Tooth Movement in Rats", Clin Oral Invest, Springer-Verlag Berlin Heidelberg, Feb. 26, 2016, 10 Pages.
Stratton, Steven A., "Role of Endorphins in Pain Modulation", The Journal of Orthopaedic and Sports Physical Therapy, vol. 3, No. 4, Mar. 24, 2017, pp. 200-205.
U.S. Patent and Trademark Office, "International Search Report and Written Opinion", PCT Application No. PCT/US2019/065839, dated Jul. 15, 2020, 14 Pages.
U.S. Patent and Trademark Office, "Non-Final Office Action Received", U.S. Appl. No. 15/147,234, filed Jan. 27, 2017, 8 Pages.
U.S. Patent and Trademark Office, "Non-Final Office Action Received", U.S. Appl. No. 15/147,234, filed Jun. 27, 2017, 20 Pages.
U.S. Patent and Trademark Office, "Non-Final Office Action Received", U.S. Appl. No. 15/791,462, filed Mar. 29, 2018, 5 Pages.
U.S. Patent and Trademark Office, "Notice of Allowance Received", U.S. Appl. No. 15/791,462, filed Apr. 30, 2019, 7 Pages.
U.S. Patent and Trademark Office, "Notice of Allowance Received", U.S. Appl. No. 15/791,462, filed Dec. 20, 2018, 7 Pages.
U.S. Patent and Trademark Office, "Notice of Allowance Received", U.S. Appl. No. 15/147,234, filed Oct. 19, 2017, 8 Pages.
Wang, "Influence of Frequency and Temperature on the Mechanisms of Nerve Conduction Block Induced by High-Frequency Biphasic Electrical Current", J Comput Neurosci., vol. 24, No. 2,, Apr. 2008, 21 Pages.
Weinberg, Seth H., "High-Frequency Stimulation of Excitable Cells and Networks", PLOS ONE, vol. 8, Issue 11, Nov. 2013, 16 Pages.
Weiss, et al., "Transcutaneous Electrical Neural Stimulation for Pain Control", Journal of Clinical Orthodontics, vol. 28, No. 11, 1994, pp. 670-671.
White, "Pain and Cooperation in Orthodontic Treatment", Journal of Clinical Orthodontics, vol. 18, No. 8, 1984, pp. 572-575.
WIPO, "International Preliminary Report on Patentability Received", PCT Application No. PCT/US2016/030922, dated Nov. 16, 2017, 7 Pages.

DEVICE FOR ELECTRICAL STIMULATION OF PERIODONTAL COMPLEX AND SURROUNDING TISSUE

CROSS-REFERENCE TO RELATED APPLICATIONS

This application is a continuation of U.S. patent application Ser. No. 15/147,234, filed May 5, 2016, pending, which is a nonprovisional application of U.S. Provisional Patent Application 62/157,053, filed May 5, 2015, which are both hereby incorporated by reference.

BACKGROUND

A significant and common side effect of orthodontic treatment is pain associated with tooth movement. Orthodontic patients experience pain during or immediately following adjustment of an orthodontic appliance, which may last from two to four days. The pain intensity ranges from a slight soreness when clenching to a constant, throbbing pain. Pain associated with orthodontic treatment is due, at least in part, to compression of a highly innervated ligament surrounding a tooth.

There are several manners and techniques used today to alleviate post-adjustment orthodontic pain. Appliances are designed using lighter wires that deliver less force to the teeth. However, many patients continue to report discomfort. Other forms of pain relief come from over the counter pharmacological drugs such as aspirin or other forms of mild analgesics. Side effects are associated with many of these drugs, and these drugs sometimes are not effective.

Another challenge in orthodontic treatment is encouraging tooth movement. The overall duration of orthodontic treatment could be reduced if teeth can be encouraged to move more quickly. There are several manners and techniques used today to attempt to encourage tooth movement, such as appliances that or apply light or vibration.

SUMMARY

This Summary introduces selected concepts in simplified form which are described further below in the Detailed Description. This Summary is intended neither to identify essential features, nor to limit the scope, of the claimed subject matter.

A device for electrical stimulation of one or more components of the periodontal complex and surrounding tissue of a tooth, for uses such as reducing orthodontic pain and encouraging tooth movement, has electrodes of a rigid, electrically conductive material in a fixed spatial relationship configured for application to oral mucosa and attached gingiva adjacent to, and along a periodontal ligament of, a root structure of a single tooth. An example of such a device is a handheld device with two electrodes which can be placed on a single tooth at a time by a patient, caretaker or care provider. Another example of such a device is an array of pairs of electrodes, shaped for application to multiple teeth, with each pair of electrodes applied to a different tooth.

With such a device, an electrical circuit is configured for electrical connection to the at least two electrodes. The electrical circuit has an output providing a subsensory electrical stimulus comprising a waveform in accordance with predetermined stimulation parameters. After the electrodes are applied to the oral mucosa and attached gingiva adjacent to, and along the periodontal ligament of, a root structure of the tooth, a switch, when activated, activates the electrical circuit to output the electrical stimulus through the at least two electrodes. The electrical circuit and/or the switch can be housed, along with the electrodes, in a single integrated housing, or can connect to a housing containing the electrodes using a variety of electrical and mechanical connections.

In one implementation, the electrical stimulus is designed for the reduction of pain associated with orthodontic tooth movement. In another implementation, the electrical stimulus is designed for encouraging cellular activity and healing of soft tissue and ligaments, to increase speed of tooth movement.

In the following description, reference is made to the accompanying drawings which form a part hereof, and in which are shown, by way of illustration, specific example implementations of this technique. It is understood that other embodiments may be utilized and structural changes may be made without departing from the scope of the disclosure.

DETAILED DESCRIPTION

The following detailed description sets forth example implementations of a device for electrical stimulation of one or more components of the periodontal complex and surrounding tissue of a tooth, for uses such as reducing orthodontic pain and encouraging tooth movement. The device has electrodes of a rigid, electrically conductive material in a fixed spatial relationship configured for application to oral mucosa and attached gingiva adjacent to, and along a periodontal ligament of, a root structure of a single tooth. An electrical circuit applies, through the electrodes, a subsensory electrical stimulus comprising a waveform in accordance with predetermined stimulation parameters. Examples of such a device described below include a handheld device with two electrodes which can be placed on a single tooth at a time by a patient, caretaker or care provider. Another example of such a device is an array of pairs of electrodes, shaped for application to multiple teeth, with each pair of electrodes applied to a different tooth.

A first example implementation of such a device will now be described in connection with FIGS. 1-3. A second example implementation of such a device is described below in connection with FIGS. 8-13. An example implementation of an electrical circuit that can be used in either implementation is described below in connection with FIGS. 4-6. A flowchart describing an example treatment process using either device is described below in connection with FIG. 7.

Figure 1:
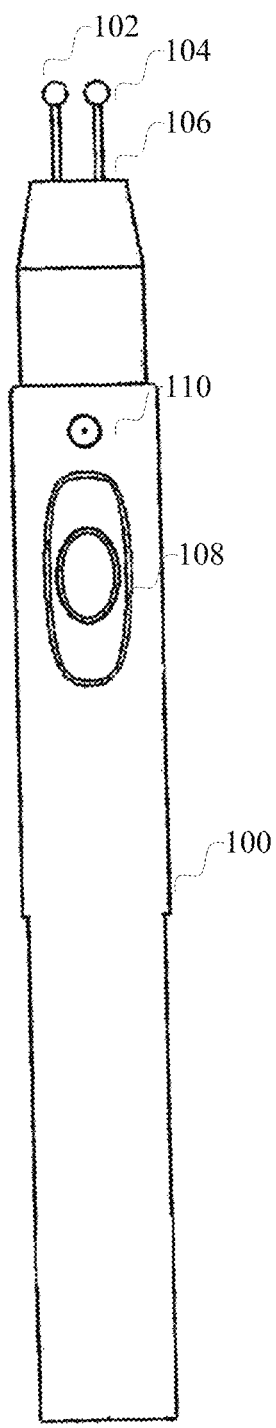
FIG. 1 is a perspective view of an example implementation of a handheld device for electrical stimulation a periodontal complex and surrounding tissue of a tooth.
Figure 4:
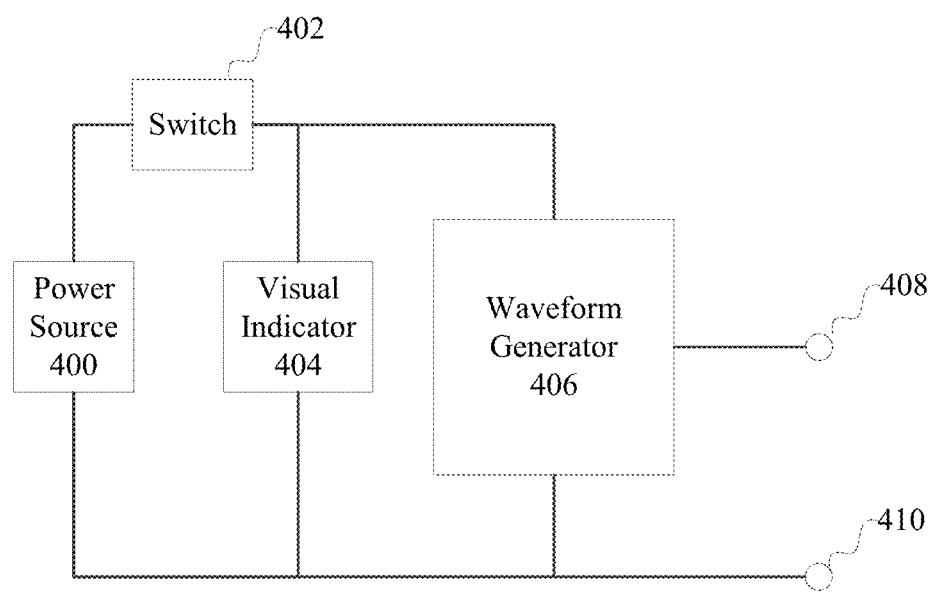
FIG. 4 is a block diagram of an example implementation of an electrical circuit that generates an electrical stimulus.

In FIG. 1, a device for electrical stimulation of the periodontal complex and surrounding tissue of a tooth includes a housing 100 configured to be handheld. At least two electrodes 102, 104 of a rigid, electrically conductive material and in a fixed spatial relationship are mounted at a first end 106 of the housing. With this example implementation, when the device is used, the electrodes of the device are manually placed on a desired location in the mouth. An electrical circuit (not shown in FIG. 1), such as described in more detail below in connection with FIG. 4, is electrically connected to the at least two electrodes 102, 104. The electrical circuit has an output providing, through the at least two electrodes, a subsensory electrical stimulus comprising a waveform in accordance with predetermined stimulation parameters. A switch 108 is provided which can be manipulated by a user to activate the electrical circuit to initiate the output of the electrical stimulus through the at least two electrodes 102, 104.

The electrical circuit and/or the switch can be housed in the housing 100 with the electrodes as shown in FIG. 1, or can connect to a housing containing the electrodes using a variety of electrical and mechanical connections. The housing can also contain a battery, or can be configured to accept an external power source through an appropriate electromechanical connection. The housing can be made of, for example, an acrylic or suitable plastic, or other solid material commonly used for similar devices. The housing can have a mating cap (not shown) to cover the electrodes when not in use.

As shown in this example implementation, a light 110, such as a light emitting diode, or other visible element, can be provided on the housing. When the electrical circuit is activated and is outputting the electrical stimulus, the light can be used to indicate operation of the device. Such a light also can be configured with the electrical circuit to indicate adequate battery power.

Figure 2:
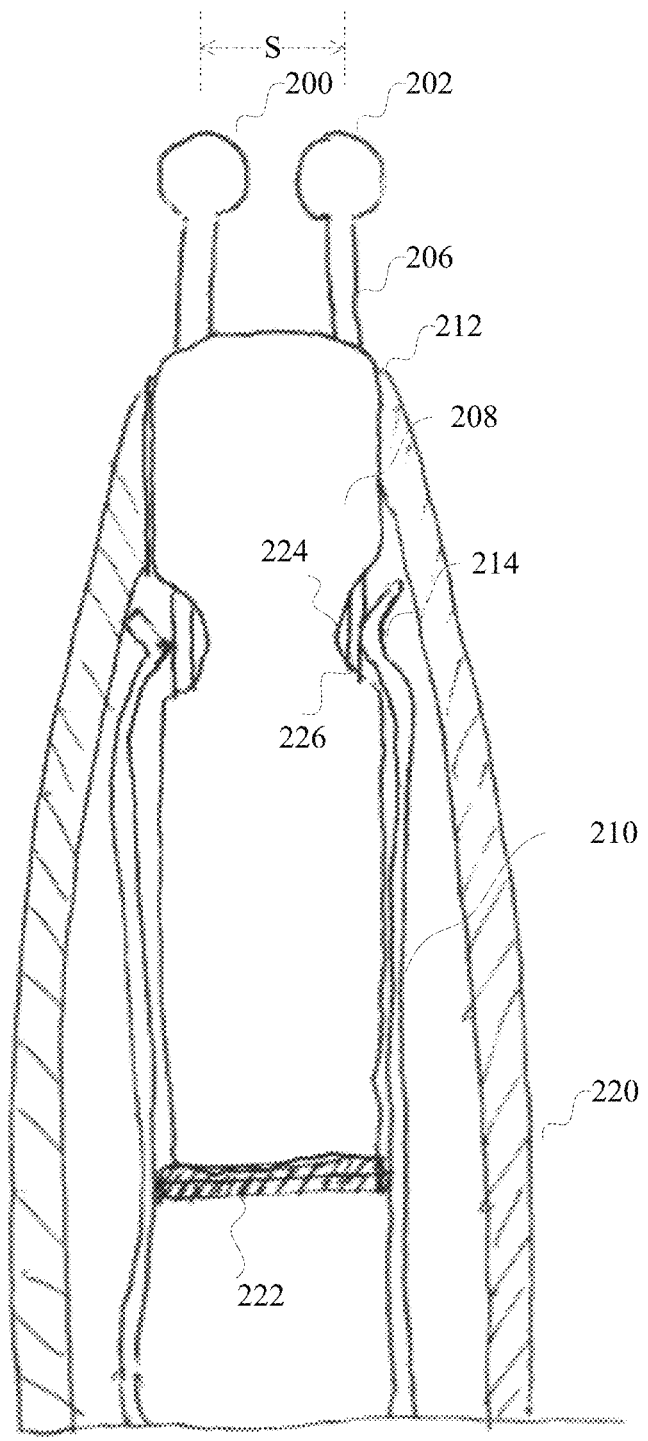
FIG. 2 is a perspective view of an example construction of electrodes for the device of FIG. 1.

In one example implementation, shown in more detail in FIG. 2, the at least two electrodes comprises two posts 206 of a rigid, electrically conductive material, such as stainless steel, connected to a base 208. While the posts 206 are illustrated as being straight, the posts can be angled to improve the ability of an operator of the device to reach teeth in the back of the mouth. The electrodes are rigid in the sense that the electrodes retain their shape and position without an external force; however, the electrodes can be made of a material than can be manipulated, shaped or bent. Several metals, such as stainless steel, are suitable for this purpose. The base can be made of ceramic or other insulating material. A tip of each post 206 can be terminated by a sphere 200, 202 of an electrically conductive material, such as stainless steel. The sphere and post of an electrode are preferably made of the same material as a single, integrated piece.

The tips of the electrodes are in a fixed spatial relationship, as indicated by spacing "S", which is based on the application of the electrodes to oral mucosa and attached gingiva adjacent to, and along a periodontal ligament of, a root structure of a single tooth, as described in more detail below in connection with FIG. 3. Thus, the spacing of the electrodes is such that they can span an adequate length along the periodontal ligament between the attached gingiva and the oral mucosa. For example, the spacing can be at least two millimeters. As another example, the spacing can be at least three millimeters. As another example, the spacing can be between two millimeters and six millimeters. As another example, the spacing can be between three and five millimeters. As another example, the spacing can be between 3.5 and 4.5 millimeters. As another example the spacing can be approximately four millimeters. In a particular example implementation as shown, each sphere can be 0.0945 inches or 2.41 mm in diameter, placed about 0.156 inches or 3.98 mm center-to-center apart.

The base 208 can have a shape corresponding to an opening 212 formed at the end of the housing 220, with the opening having a bottom portion 222, and the base 208 can be configured to be removable. With such a construction, the base has a first mechanical connector having a mating configuration with a second mechanical connector of the housing; the base also has a first electrical connection having a mating configuration with a second electrical connection of the housing. Such a construction of the housing and electrode interconnection allows for removal of the electrodes for cleaning or sterilization, for replacement, or to allow various configurations of electrodes to be used.

In the example shown in FIG. 2, the base can engage electrically conductive connectors, e.g., 210, which provide for mechanical engagement of the base 208 with the housing 220, and an electrical connection to a circuit (not shown in FIG. 2) within the housing. The circuit within the housing provides for the electrical connection to the electrical circuit that generates the electrical stimulus. More particularly, in the example shown in FIG. 2, a bent portion 214 of the connector 210 engages an area of the base 208 that forms a gap 224 to provide mechanical engagement; the bent portion 214 also contacts a portion 226 of the post 206 to provide the electrical connection.

Figure 3:
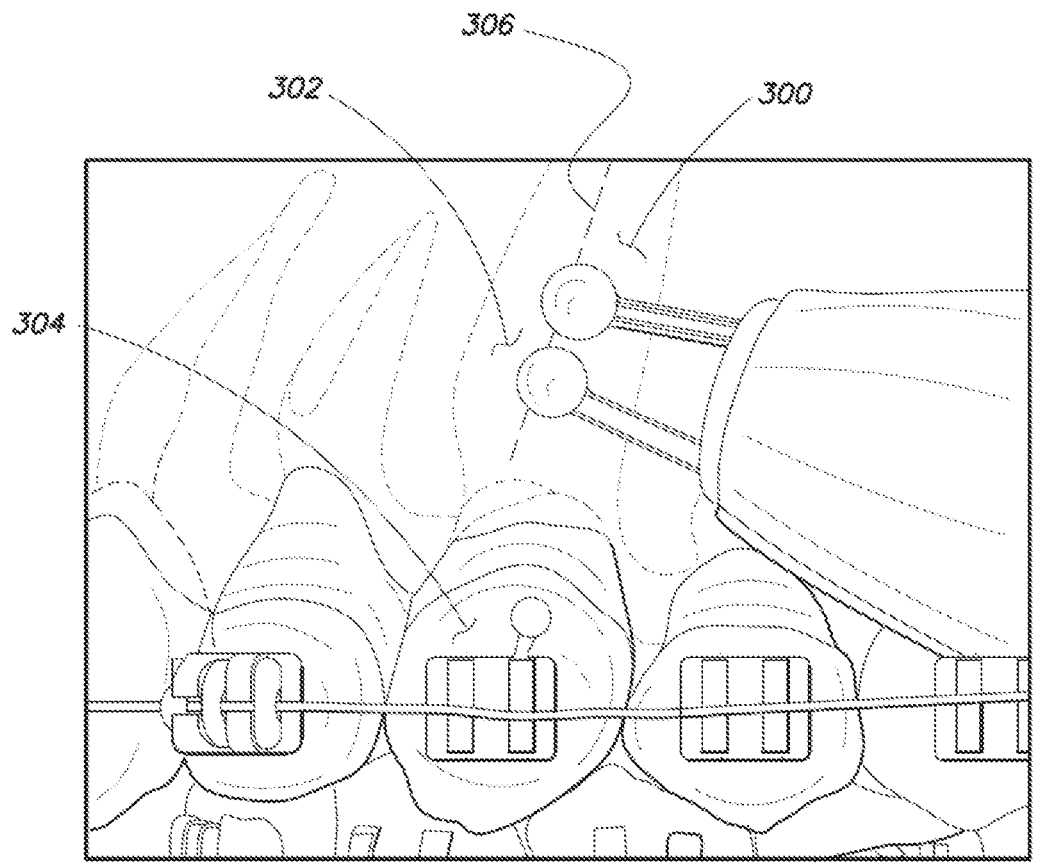
FIG. 3 is a perspective view illustrating electrode placement on oral mucosa and attached gingiva adjacent to, and along a periodontal ligament of, a root structure of a tooth.

Turning now to FIG. 3, placement of the electrodes will now be described in more detail. While FIG. 3 illustrates application of the electrodes to a facial surface, the electrodes can be placed on any surface of the tissue surrounding the periodontal complex, whether facial, palatal, lingual or buccal surfaces. In use, the two electrodes are placed on oral mucosa 300 and attached gingiva 302 adjacent to, and along (as indicated by dashed line 306) a periodontal ligament of, a root structure of a single tooth 304. When the electrical stimulus is applied from the electrical circuit through the electrodes so placed on a tooth, the device electrically stimulates one or more components of the periodontal complex (which includes the tooth, its root nerve, periodontal ligament, and bone) and its surrounding tissue (including gingiva and oral mucosa) of the tooth. Such direct electrical stimulation of one or more components of the periodontal complex and surrounding tissue of the tooth, which includes both a highly innervated ligament that can become compressed and soft tissue which can be damaged by orthodontic adjustments and tooth movement, can stimulate the various pathways or mechanisms that relate to pain and/or increased cellular activity.

Turning now to FIG. 4, an example implementation of an electrical circuit will now be described. In FIG. 4, the electrical circuit includes a power source 400, such as a battery. As an alternative to a battery, an external power source can be used. A battery can include one or more batteries, such as button cell batteries. In one example implementation, a 4.5 volt direct current source can be provided by three 1.5 volt button cell batteries.

A switch 402 is used to activate the electrical circuit. For example, the switch 402 can represent a button switch such as shown on the device in FIG. 1. The switch 402 can include any of a variety of mechanical switches, an electromechanical switch, or an electrical switch. The switching function can be provided by a control signal from an external controller.

The electrical circuit can include a visual indicator 404, such as a light emitting diode, to indicate whether the electrical circuit is active. The visual indicator also, or alternatively, can be selected, and the electrical circuit can be designed, so as to indicate battery level or other operational state of the device.

The electrical circuit also includes a waveform generator 406. The waveform generator is a circuit that generates an electrical stimulus comprising a waveform in accordance with predetermined stimulation parameters. The output of the waveform generator is applied through electrodes 408 and 410. The design of the electrical circuit is dependent on an output waveform and other stimulation parameters defining the electrical stimulus to be generated for a particular application. The predetermined stimulation parameters include at least a form of the output waveform, a pulse frequency of the waveform, and a current. A duration of the electrical stimulus also can be predetermined. The waveform generator is designed to provide the output waveform according to its specified form and pulse frequency. Given a voltage that powers the electrical circuit (which may be a nominal voltage if a battery is used as a power source), a resistance in series with the output of the waveform generator is selected to provide the desired output current.

By having a device with predetermined stimulation parameters, the electrical stimulus can be ensured to be subsensory and in a form for its desired purpose. With such a configuration, patients can safely use the device.

The duration and/or frequency of application of the electrical stimulus also can be controlled by the electrical circuit. For example, the electrical circuit can include one or more timers (not shown in FIG. 4). Such timers can further control activation and deactivation of the electrical circuit so that the electrical circuit outputs the electrical stimulus only for a specified duration. Such timers also can further control activation of the electrical circuit so that it cannot be reactivated until a specified period of time has elapsed. In most applications, the duration of a single application is an amount of time greater than ten seconds and less than twenty minutes.

Generally speaking the electrical stimulus should be subsensory and therapeutically effective for reducing orthodontic pain and/or encouraging tooth movement.

The electrical stimulus is sub-sensory when the voltage and current applied are sufficiently low that there is no sensory perception of the electrical stimulus by the patient. The electrical stimulus is generally subsensory at a current of less than 10 milliamperes.

The electrical stimulus is therapeutically effective depending on the biological mechanism by which analgesia is produced or by which cellular response is stimulated. While research has demonstrated that such effects occur in humans in response to certain electrical stimuli, the precise biological mechanisms through which analgesic effects or cellular activity occurs in response to electrical stimulation is not well known. In some cases, A-delta and A-beta fibers may be stimulated to block transmission of painful stimuli by small unmyelinated C-fibers in the spinal cord. A-beta fibers appear to be best stimulated at a frequency in the range of about 80 Hz to 130 Hz; A-delta fibers appear to be best stimulated at a frequency in the range of about 2 Hz to 10 Hz, and more particularly 2 Hz to 5 Hz. Both types of fibers also appear to be stimulated with a burst mode high frequency (e.g., greater than 100 Hz) signal interrupted at a rate of about two to three bursts per second. In some cases, an endorphin mediated mechanism may be activated by the electrical stimulus. Yet other biological mechanisms may be effected by electrical stimulation, such as prevention of formation of neural pathways which may otherwise form in response to pain in the absence of such electrical stimulation.

As a particular example, a waveform with a pulse frequency of less than 12 kHz and greater than 0.5 Hz, applied with a current in the range of 20 microamperes to ten milliamperes, can be therapeutically effective for pain reduction with an application time of as little as ten seconds up to about several minutes per tooth. More particularly, the frequency range can be between 100 Hz and 12 kHz. More particularly, the frequency range can be between 1 kHz and 12 kHz. More particularly, the current range can be between 1 milliampere and 10 milliamperes. More particularly, the current range can be between 5 milliamperes and 10 milliamperes. Such an electrical stimulus can be applied whenever a patient senses pain after an orthodontic adjustment. Such treatment typically would be applied once a day only for one to four days after an orthodontic adjustment. Orthodontic patients could receive a treatment immediately following any procedure that may cause discomfort. At such a low level of current, there is no sensory perception, and is safe for a wide range of patients including children.

As another example, for encouraging tooth movement, a waveform with a pulse frequency of less than 12 kHz and greater than 0.5 Hz, with a current of approximately 20 microamperes to 800 microamperes, and more particularly 20 microamperes to 200 microamperes can be therapeutically effective with an application time of between about 10 minutes and 20 minutes, for example about 15 minutes. The effective frequency is dependent on the teeth being moved, because bone density is greater in the mandibular arch than in the maxillary arch. Such an electrical stimulus can be applied several times a day, such as two to four times a day, over a period of several days, such as one to fourteen days.

Figure 5:
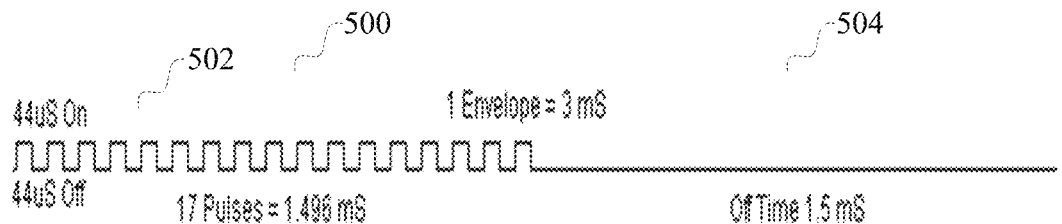
FIG. 5 is an illustration of an example waveform that can be used as an electrical stimulus.
Figure 6:
FIG. 6 is a further illustration of the example waveform.

In one implementation, as an example, the electrical stimulus comprises a waveform as shown in FIGS. 5 and 6. This waveform includes a plurality of envelopes, where each envelope 500 includes a plurality of pulses 502 at a pulse frequency, followed by an off time 504. While FIG. 5 shows the form of the output waveform as a rectangular waveform, pulses can be sloped, e.g., triangular, or curved, e.g., sinusoidal. An envelope can have a positive or negative polarity, i.e., either positive or negative peak voltage. A plurality of such envelopes can be repeated in a sequence, thus providing an envelope frequency.

As a specific example of such a waveform, pulses of 44 microseconds on followed by 44 microseconds off provide a total pulse width of 88 microseconds, and a pulse frequency of about 11363.6 Hz. With 17 such pulses, followed by an off time of 1.5 milliseconds, in one envelope, the envelope time is about three (3) milliseconds, providing an envelope frequency of about 333.3 Hz.

The waveform can include a plurality of envelopes at a first, e.g., positive, polarity, followed a plurality of envelopes at a second, e.g., negative, polarity. In the implementation shown in FIG. 6, the waveform includes 333 envelopes at a positive peak voltage, followed by 333 envelopes at a negative peak voltage, to provide one (1) second of a positive signal and one (1) second of a negative signal. The frequency of the positive to negative signal transition is thus 0.5 Hz.

With the waveform such as shown in FIGS. 5 and 6, and a nominal battery voltage powering the electrical circuit of about 4.5 volts, and an output resistance of 440 ohms, a nominal output current of about 10 milliamps can be provided.

Figure 7:
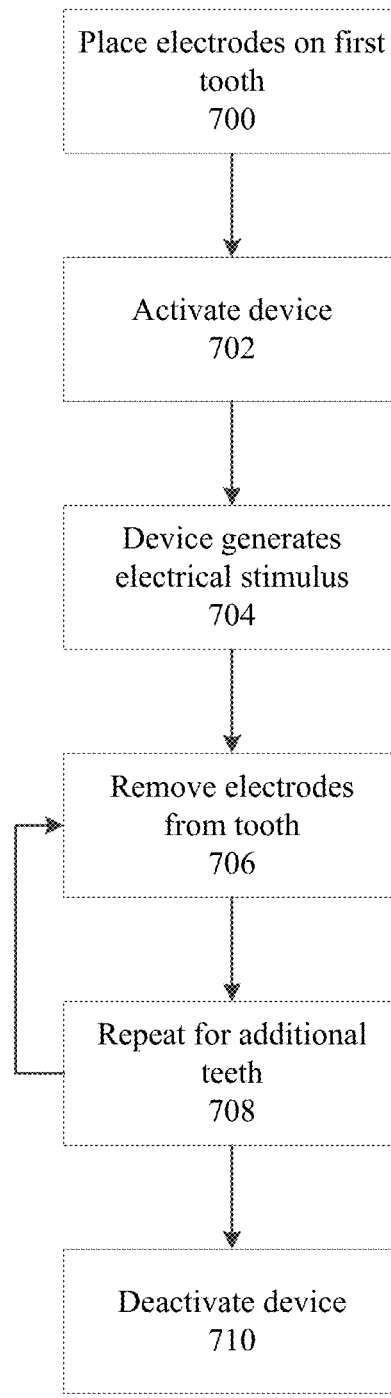
FIG. 7 is a flow chart describing an example process of treatment using such a device.

Turning now to FIG. 7, a flow chart describing an example treatment procedure using such a device will now be described. This treatment process can be performed by an orthodontist or other health care provider, the patient, or a patient's caretaker or parent. Because the device generates a fixed, subsensory electrical stimulus, this process can even be performed by a child patient. After a patient has received an orthodontic adjustment, pain may be present in one or more teeth. To reduce pain experienced for a tooth, first the electrodes of the device are placed 700 on oral mucosa and attached gingiva adjacent to, and along a periodontal ligament of, a root structure of a single tooth, such as shown in FIG. 3. The electrical circuit for the device is then activated 702, for example by pressing a button of a device such as shown in FIG. 1. The device generates 704 the electrical stimulus, which is applied through the electrodes to the oral mucosa and attached gingiva adjacent to, and along the periodontal ligament of, the root structure of the tooth on which the electrodes have been placed. After a period of time, such as about ten seconds, the electrodes can be removed 706 from the tooth. The electrodes can be placed on another tooth, as indicated at 708, to apply the electrical stimulus to the other tooth, which can be repeated for multiple other teeth.

Figure 8:
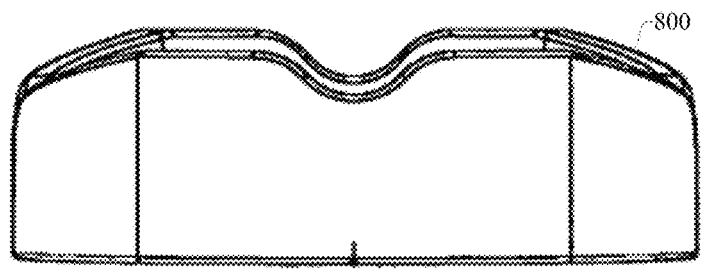
FIG. 8 is front elevation of another example implementation of a device having an array of electrodes.

Referring now to FIGS. 8-13, a second example of an implementation of such a device for electrical stimulation of one or more components of a periodontal complex and surrounding tissue of multiple teeth, will now be described. In this implementation, an array of pairs of electrodes is used to apply electrical stimulation to components the periodontal complexes of multiple teeth. Such an array is particularly useful for encouraging tooth movement throughout the entire mouth, but also can be used for pain reduction. In this device, the principle of electrical stimulation, the stimulation parameters of the electrical stimulus used for treatment, and corresponding electrical circuit for generating the electrical stimulus, are similar to those of a device for treating a single tooth. In FIG. 8, an array of electrodes can deliver the electrical stimulus to multiple teeth. The electrical circuit can be designed to drive all pairs of electrodes simultaneously, or all pairs of electrodes in a subset can be driven simultaneously with each subset being driven in sequence, or individual pairs of electrodes can be driven in sequence, or an individual pair of electrodes can be selected and driven with the electrical stimulus.

Figure 9:
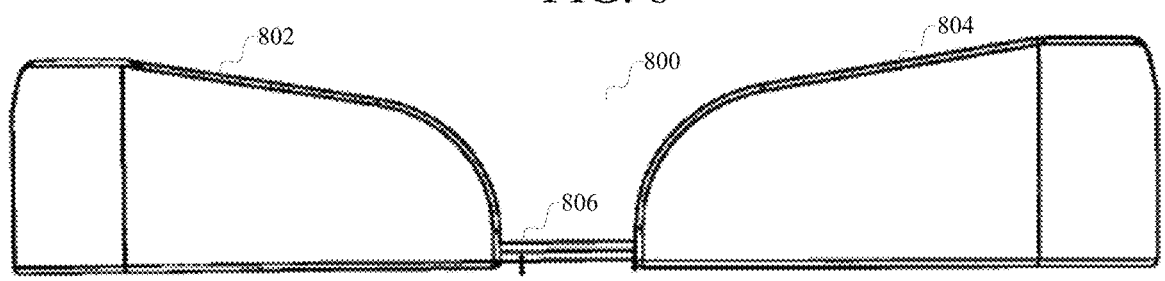
FIG. 9 is a side elevation of the implementation of FIG. 8.
Figure 10:
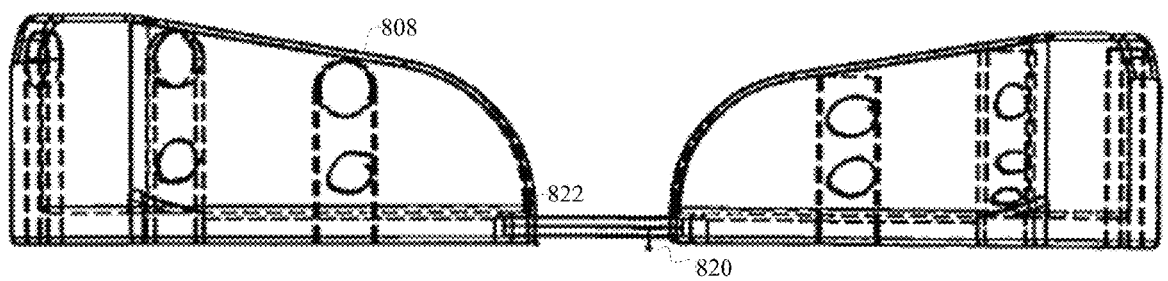
FIG. 10 is a side cross-sectional view of the implementation of FIG. 8.
Figure 11:
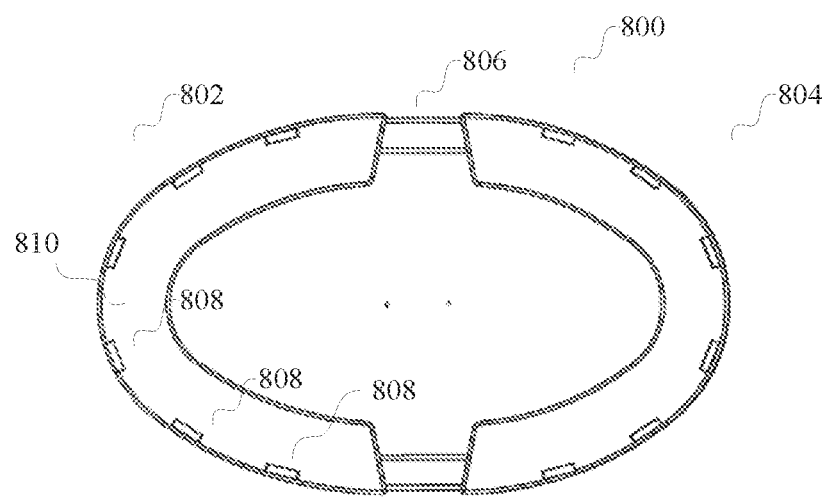
FIG. 11 is a top plan view of the implementation of FIG. 8.
Figure 12:
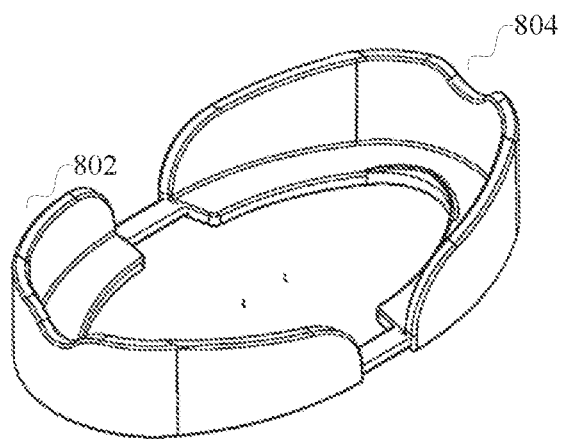
FIG. 12 is a top perspective view of the implementation of FIG. 8.
Figure 13:
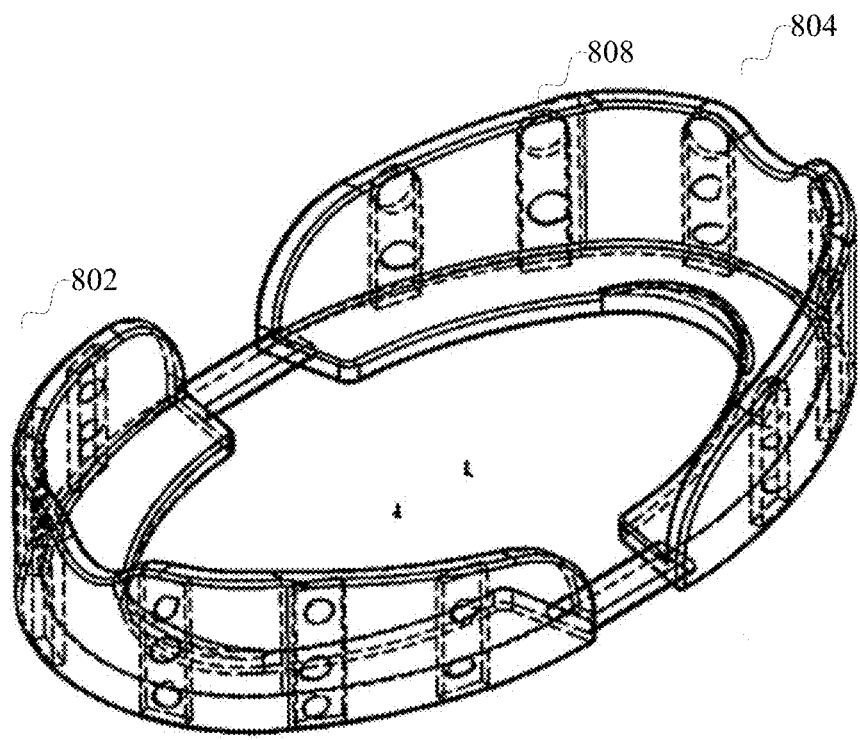
FIG. 13 is a top perspective cross-sectional view of the implementation of FIG. 8.

FIG. 8 is front elevation of this example implementation of the device having an array of electrodes. FIG. 9 is a side elevation of the example implementation of FIG. 8. FIG. 10 is a side cross-sectional view of the example implementation of FIG. 8. FIG. 11 is a top plan view of the example implementation of FIG. 8. FIG. 12 is a top perspective view of the example implementation of FIG. 8. FIG. 13 is a top perspective cross-sectional view of the example implementation of FIG. 8.

In this example implementation of the device, a housing 800 is shaped to be placed around teeth along a jaw of a patient. The housing can be designed to encapsulate the electromechanical components in a hermetic package made from biocompatible materials suitable for long term intraoral use. In this example implementation, the housing has a first portion 802 for a top set of teeth, and a second portion 804 for a bottom set of teeth. A flexible portion 806 allows the device to be folded for placement in the mouth. A plurality of pairs 808 of electrodes in a fixed spatial relationship are mounted at locations along an internal face 810 of the housing corresponding to positions of the teeth along the jaw. The electrodes shown in this example implementation are in the form small hemispherical objects of electrically conductive material, such as stainless steel, and having a substantially flat surface facing the soft tissue to which they will be applied. Such electrodes can be about the same size as the spheres shown above in FIG. 2. When the housing is placed in the mouth and surrounding the teeth along the jaw, each pair of electrodes is placed in contact with oral mucosa and attached gingiva adjacent to, and along a periodontal ligament of, a root structure of its corresponding tooth. An electrical circuit, such as shown in FIG. 4, is connected to the housing 800 through an electromechanical interface 820 and wires 822 to deliver the electrical stimulus to the pairs of electrodes.

Such a device also can be configured for long term placement during orthodontic treatment. Electrodes can be placed, and then connected via wires to a device containing the electrical components that generate the desired electrical stimulus.

Other implementations of devices providing electrical stimuli include arrays shaped as a pacifier on which pairs of electrodes are placed at spacings corresponding to individual teeth, such as in an infant's or toddler's mouth. Such a device can help relieve teething or tooth eruption pain of small children.

There are several additional benefits to a patient from using a device such as described herein in connection with orthodontic treatment to electrically stimulate components of the periodontal complex affected by the orthodontic treatment. For example, a reduction in pain experienced by a patient may lead the patient to have better oral hygiene and compliance with other instructions of the orthodontist. Also, many patients may otherwise avoid orthodontic treatment because of pain that is known to be associated with such treatment. The ability to offer more comfortable orthodontic treatment may enable an orthodontist to provide services for previously apprehensive patients. The use of electrical stimulation for pain reduction also may decrease the amount of analgesics consumed by patients. Also, to the extent that electrical stimulation is used in orthodontic treatment to encourage tooth movement and/or tissue growth, such stimulation may improve the healing time associated with tooth movement and may reduce overall treatment time.

Pain relief, stimulation of cellular response, and increased healing rates are not limited to orthodontic treatment. Such a device also can be used to reduce pain and improve healing times for other conditions and/or procedures that affect components of the periodontal complex, such as dental conditions and procedures, endodontic conditions and procedures, implants, and other oral surgery.

It should be understood that the subject matter defined in the appended claims is not necessarily limited to the specific implementations described above. The specific implementations described above are disclosed as examples only.

What is claimed is:

1. A device for electrical stimulation of one or more components of a periodontal complex and surrounding tissue of a tooth, comprising:
a housing configured to be handheld;
at least two electrodes of a rigid, electrically conductive material, wherein the at least two electrodes are mounted in a fixed spatial relationship at an end of the housing and have a spacing between them, wherein the housing and the spacing between the at least two electrodes are such that the at least two electrodes are configured for application to be applied to oral mucosa and attached gingiva adjacent to, and along a periodontal ligament of, a root structure of a single tooth;
an electrical circuit configured for electrical connection to the at least two electrodes, the electrical circuit having an output providing a subsensory an electrical stimulus comprising a waveform in accordance with predetermined stimulation parameters; and
a switch configured to activate the electrical circuit such that, when the switch is activated when the electrodes are applied to the oral mucosa and attached gingiva adjacent to, and along the periodontal ligament of, the root structure of the single tooth, the switch activates the electrical circuit to output the electrical stimulus through the at least two electrodes.

2. The device of claim 1, wherein the at least two electrodes comprise:
a base having a first mechanical connector and a first electrical connection, wherein the at least two electrodes are mounted in the base; and wherein the housing has a second mechanical connector having a mating configuration with the first mechanical connector of the base and a second electrical connection having a mating configuration with the first electrical connection of the base; whereby the base is removably connectable to the housing.

3. The device of claim 1, wherein the electrical circuit is mounted in the housing and wherein the output of the electrical circuit is connected to the second electrical connection of the housing.

4. The device of claim 1, wherein the switch is mounted on the housing.

5. The device of claim 1, wherein the switch is a mechanical switch or an electromechanical switch or a controller configured to activate the electrical circuit.

6. The device of claim 1, wherein the electrical stimulus is a therapeutically effective electrical stimulus for a periodontal complex of a tooth.

7. The device of claim 1, wherein the electrical stimulus is a therapeutically effective electrical stimulus for increasing tooth movement.

8. The device of claim 1, wherein the electrical stimulus is a therapeutically effective electrical stimulus for relieving periodontal pain.

9. The device of claim 1, wherein the waveform comprises a plurality of pulses having a pulse frequency.

10. The device of claim 9, wherein the waveform comprises a first plurality of pulses of a positive polarity at the pulse frequency in a first envelope, and a second plurality of pulses of a negative polarity at the pulse frequency in a second envelope, and a transition between the first and second envelopes occurring at a transition frequency.

11. The device of claim 9, wherein the pulse frequency is in a range of 1 kHz to 12 kHz.

12. The device of claim 10, wherein the predetermined stimulation parameters comprise a current of the electrical stimulus, and wherein the current is less than ten milliamperes.

13. The device of claim 11, wherein the predetermined stimulation parameters comprise a duration of the electrical stimulus, and wherein the duration is an amount of time greater than ten seconds and less than twenty minutes.

14. A device for electrical stimulation of one or more components of a periodontal complex and surrounding tissue of a tooth, comprising:
at least two electrodes of a rigid, electrically conductive material, wherein the at least two electrodes are mounted on a base in a fixed spatial relationship and have a spacing between them, wherein the spacing between the at least two electrodes are such that the at least two electrodes are configured to be applied to oral mucosa and attached gingiva adjacent to, and along a periodontal ligament of, a root structure of a single tooth;
an electrical circuit electrically connected to the at least two electrodes, the electrical circuit having an output to the at least two electrodes providing an electrical stimulus comprising a waveform in accordance with predetermined stimulation parameters; and
a switch connected to the electrical circuit such that, when the switch is activated when the electrodes are applied to the oral mucosa and attached gingiva adjacent to, and along the periodontal ligament of, the root structure of the single tooth, the switch activates the electrical circuit to output the electrical stimulus through the at least two electrodes.

15. The device of claim 13, wherein the waveform comprises a plurality of pulses having a pulse frequency.

16. The device of claim 14, wherein the pulse frequency is in a range of 1 kHz to 12 kHz.

17. The device of claim 15, wherein the predetermined stimulation parameters comprise a current of the electrical stimulus, and wherein the current is less than ten milliamperes.

18. The device of claim 16, wherein the predetermined stimulation parameters comprise a duration of the electrical stimulus, and wherein the duration is an amount of time greater than ten seconds and less than twenty minutes.

* * * * *